United States Patent
Covey et al.

(10) Patent No.: US 7,069,074 B2
(45) Date of Patent: Jun. 27, 2006

(54) EASY-TO-USE ELECTRODE AND PACKAGE

(75) Inventors: Kevin Kelly Covey, Marysville, WA (US); Kelly JoAnn Locke, Woodinville, WA (US); Shawn Robert Bertagnole, Lake Stevens, WA (US)

(73) Assignee: Medtronic Emergency Response Systems, Inc., Redmond, WA (US)

( * ) Notice: Subject to any disclaimer, the term of this patent is extended or adjusted under 35 U.S.C. 154(b) by 376 days.

(21) Appl. No.: 10/008,243

(22) Filed: Nov. 7, 2001

(65) Prior Publication Data

US 2003/0088276 A1   May 8, 2003

(51) Int. Cl.
*A61N 1/362* (2006.01)
(52) U.S. Cl. .......................................... 607/5
(58) Field of Classification Search ................ 607/2–7, 607/142, 108; 206/210, 305; 429/131, 136; 128/898; 229/123.3; 383/5, 9
See application file for complete search history.

(56) References Cited

U.S. PATENT DOCUMENTS

| | | | | |
|---|---|---|---|---|
| 3,407,818 A | * | 10/1968 | Costanzo | 607/108 |
| 3,685,645 A | * | 8/1972 | Kawaguchi | 206/210 |
| 3,930,580 A | | 1/1976 | Bazell et al. | |
| 4,420,078 A | * | 12/1983 | Belt et al. | 206/305 |
| 4,559,950 A | | 12/1985 | Vaughan et al. | |
| 4,566,129 A | * | 1/1986 | McNamee | 383/5 |
| 4,858,821 A | | 8/1989 | Bickelhaupt | |
| 4,986,465 A | * | 1/1991 | Jacobsson et al. | 229/123.3 |
| 5,311,990 A | | 5/1994 | Kalinski | |
| 5,356,428 A | | 10/1994 | Way | |
| 5,366,497 A | | 11/1994 | Ilvento et al. | |
| 5,419,450 A | | 5/1995 | Guglielmelli et al. | |
| 5,456,710 A | | 10/1995 | Gadsby | |
| 5,459,978 A | | 10/1995 | Weiss et al. | |
| 5,462,157 A | * | 10/1995 | Freeman et al. | 206/210 |
| 5,466,244 A | | 11/1995 | Morgan | |
| 5,520,760 A | | 5/1996 | Freedman | |
| 5,591,213 A | | 1/1997 | Morgan | |
| 5,617,853 A | | 4/1997 | Morgan | |
| 5,697,955 A | | 12/1997 | Stolte | |
| 5,772,690 A | * | 6/1998 | Kroll | 607/7 |
| 5,792,190 A | | 8/1998 | Olson et al. | |
| 5,807,619 A | | 9/1998 | Freedman | |
| 5,817,151 A | | 10/1998 | Olson et al. | |
| 5,842,567 A | | 12/1998 | Rowe et al. | |
| 5,908,245 A | * | 6/1999 | Bost et al. | 383/9 |
| 5,916,244 A | | 6/1999 | Walters | |
| 5,951,598 A | | 9/1999 | Bishay et al. | |
| 6,048,640 A | * | 4/2000 | Walters et al. | 429/136 |
| 6,059,111 A | | 5/2000 | Davila et al. | |

(Continued)

OTHER PUBLICATIONS

"Survivalink / FirstSave AED" http://www.survivalink.com/see/index.html.

(Continued)

*Primary Examiner*—George Manuel
(74) *Attorney, Agent, or Firm*—Shumaker & Sieffert, P.A.

(57) ABSTRACT

The invention presents techniques for making the operation of an automated external defibrillator easier to understand for an operator. The automated external defibrillator includes defibrillation electrodes packaged in a sealed, easy-to-open pouch. Visual cues such as instructive pictures show the operator how to open the pouch, retrieve the defibrillation electrodes and correctly position the electrodes on a patient's chest.

17 Claims, 4 Drawing Sheets

U.S. PATENT DOCUMENTS

| | | | |
|---|---|---|---|
| 6,097,987 A | 8/2000 | Milani | |
| 6,115,638 A | 9/2000 | Groenke | |
| 6,117,505 A | 9/2000 | Weiss et al. | |
| 6,178,357 B1 | 1/2001 | Gliner et al. | |
| 6,223,088 B1 | 4/2001 | Scharnberg et al. | |
| 6,272,385 B1 | 8/2001 | Bishay et al. | |
| 6,334,070 B1 | 12/2001 | Nova et al. | |
| 6,611,709 B1* | 8/2003 | Faller et al. | 607/5 |
| 6,675,051 B1* | 1/2004 | Janae et al. | 607/142 |
| 2003/0114885 A1* | 6/2003 | Nova et al. | 607/2 |

OTHER PUBLICATIONS http://www.voltek.com/defibrillator.html.

"Product Sheets" http://www.zoll.com/hospshts.htm.

"Automatic External Defibrillator—AED" http://www.lifesafety.com/erkits/defib.htm.

U.S. Appl. No. 09/970,079, filed Oct. 2, 2001, Entitled: System and Device for Implementing an Integrated Medical Device Component Package.

* cited by examiner

EASY-TO-USE ELECTRODE AND PACKAGE

FIELD

The invention relates to medical devices for treating cardiac conditions, and more particularly, to external defibrillators.

BACKGROUND

Cardiac arrest is a life-threatening medical condition that may be treated with external defibrillation. External defibrillation includes applying electrodes to the patient's chest and delivering an electric shock to the patient to depolarize the patient's heart and restore normal sinus rhythm. The chances that a patient's heart can be successfully defibrillated increase significantly if a defibrillation pulse is applied quickly.

Until recently, individuals such as paramedics, emergency medical technicians, police officers and others trained in defibrillation techniques used defibrillators, but the general public did not. In some cases, the patient's need is urgent and the patient cannot wait for trained personnel to arrive. In recognition of the need for prompt treatment, automated external defibrillators (AED's) are becoming more commonplace, and are available in venues such as airports, health clubs and auditoriums.

When an AED is used to treat a patient, much of the treatment is performed by the AED rather than the person who operates the AED. In general, the AED automatically measures the patient's cardiac signals, assesses whether a shock is indicated and charges a storage element in preparation for giving the shock. When a shock is indicated, the AED may cue the operator to administer the shock, or the AED may administer the shock automatically. In addition, many AED's include visual displays, voice instructions and other audible messages that tell the operator about the status of the defibrillator.

Placement of defibrillation electrodes on the patient's chest, however, cannot be performed by the AED. In many AED's, the electrodes are packaged in a sealed pouch. The operator must open the pouch, retrieve the electrodes and place the electrodes in the correct positions on the patient's chest. In many cases, a minimally trained operator, properly instructed, can place the electrodes on the patient's chest in the correct positions. Without instruction, the operator could put one or both electrodes in an incorrect anatomical placement.

SUMMARY

The invention is directed to making an AED more effective when used by an operator, such as a minimally trained operator who operates the AED infrequently. Because time is at a premium, an operator should be able to understand how to use an AED with as little instruction as possible. In particular, an operator should be able to find the electrode pouch immediately, open the pouch in moments, and to place the electrodes in the correct positions quickly and accurately. The invention is directed toward helping an operator apply defibrillation therapy to a patient, when time is of the essence.

In one embodiment, the invention presents a medical device, such as a defibrillator or defibrillator-monitor, with a pouch containing a defibrillation electrode fastened to the medical device. The pouch may be fastened to the medical device with an anchor. The pouch may further include a handle. By pulling the handle, the operator easily opens the pouch to retrieve the electrodes. Instructive pictures and other visual cues may further help the operator understand how to open the pouch and how to place the electrodes.

In another embodiment, the invention presents a pouch containing a defibrillation electrode. The pouch includes a handle that an operator pulls, causing the pouch to open. The handle may have, for example, a ring shape and may be a distinctive color. A notch in the pouch may help the operator to tear open the pouch. The invention also encompasses a method of making such a pouch.

In a further embodiment, the invention presents defibrillation electrodes with instructive pictures. The instructive pictures show a human figure with electrode symbols, to instruct the operator as to where and how to place the electrodes. The instructional picture on an electrode is printed at an angle. When the operator applies the defibrillation electrode to the patient, with the head of the patient and the head of the human figure in the same direction, the defibrillation electrode will be oriented at a proper angle.

Many of the features of the invention are directed to saving time, and thereby increasing the patient's chances of survival. Although the invention is advantageous to those with experience with AED's, the invention is particularly of benefit to operators who have little formal training in the use of the AED or may have had training a long time ago. The invention provides visual cues that show the operator what to do. The visual cues are easy to understand and the actions to be performed are easy to do. By following the visual cues, the operator can quickly retrieve the packaged electrodes and place the electrodes at the proper locations on the patient.

The above summary of the invention is not intended to describe every embodiment of the invention. The details of one or more embodiments of the invention are set forth in the accompanying drawings and the description below. Other features, objects, and advantages of the invention will be apparent from the description and drawings, and from the claims.

DETAILED DESCRIPTION

Figure 1:
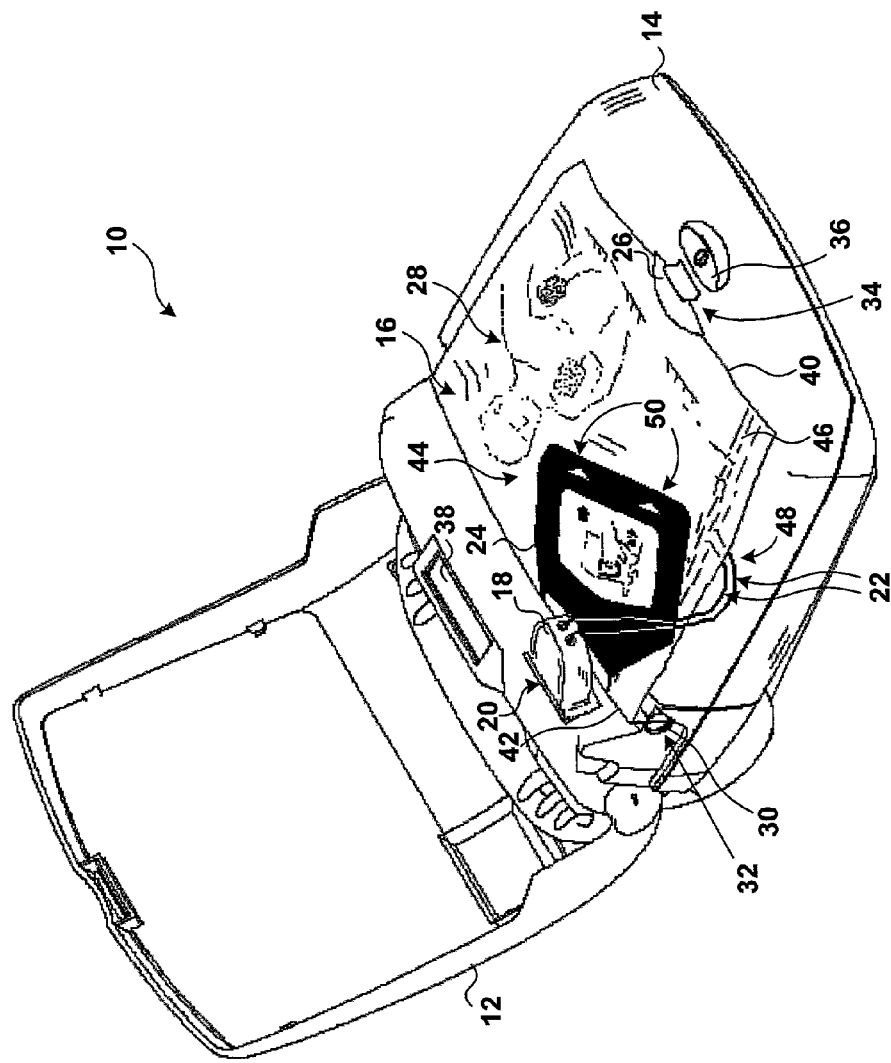
FIG. 1 is a perspective view of an AED.

FIG. 1 shows an example medical device that illustrates an embodiment of the invention. AED 10 includes cover 12, which is hingedly coupled to defibrillator case 14. Defibrillator case 14 includes circuitry (not shown in FIG. 1) that performs functions such as making measurements, processing cardiac signals, storing energy for delivery as a defibrillation pulse and regulating the delivery of the defibrillation pulse. Defibrillator case 14 also houses a power supply such as a battery (not shown in FIG. 1). In addition, defibrillator case 14 may include circuitry that controls automated voice instructions, other audible messages and readiness indicators and other visual indicators 38.

Pouch 16 rests atop defibrillator case 14. In one example, pouch 16 is about 7.3 in (18.5 cm) wide and 5.7 in (14.5 cm) long. Pouch 16 contains electrodes 74 and 76 (not shown in FIG. 1) to be placed upon the chest of the patient. Electrodes 74 and 76 are electrically coupled to defibrillator case 14 via insulated lead wires 22 and connector 18. Lead wires 22 extend from electrodes 74 and 76 through sealed entry point 48 in pouch 16, and are coupled to connector 18. Connector 18 mates to receptacle 20 in defibrillator case 14. Signals detected by electrodes 74 and 76 are supplied to processors in defibrillator case 14 via insulated lead wires 22 and connector 18. Similarly, defibrillation pulses are supplied from energy storage circuitry in defibrillator case 14 to electrodes 74 and 76 via connector 18 and insulated lead wires 22.

Pouch 16 is fastened to defibrillator case 14. In the example embodiment shown in FIG. 1, cylindrical slot 32 in defibrillator case 14 receives cylindrical member 30. Cylindrical member 30 is a component of pouch 16 located near upper left corner 42 of pouch 16. As will be shown below, cylindrical member 30, when engaged with cylindrical slot 32, serves as an anchor for pouch 16. The placement of cylindrical slot 32 and cylindrical member 30 contribute to making pouch 16 easy to open. In addition, the placement of cylindrical slot 32 and cylindrical member 30 assure that pouch 16 is fastened to defibrillator case 14 with obverse face 44 of pouch 16 exposed.

Defibrillator case 14 includes lip 26. Bottom edge 40 of pouch 16 is tucked beneath lip 26. Together, cylindrical slot 32 and lip 26 help keep pouch 16 in place.

Electrodes 74 and 76 and pouch 16 are not permanently coupled to defibrillation case 14, and it is advantageous for electrodes 74 and 76 and pouch 16 to be removable. Pouch 16 typically has a shelf life, for example, and electrodes 74 and 76 and pouch 16 are replaced when the shelf life expires. In addition, electrodes 74 and 76 and pouch 16 are replaced after pouch 16 has been opened.

Accordingly, connector 18 may be decoupled from receptacle 20 by pulling connector 18 from receptacle 20. Pouch 16 may be decoupled from defibrillator case 14 by sliding cylindrical member 30 out of cylindrical slot 32 and, if necessary, by pulling pouch 16 from under lip 26. Installing new electrodes and pouch 16 comprises obtaining a fresh, unopened pouch 16, inserting cylindrical member 30 into cylindrical slot 32, tucking lower edge 40 of pouch 16 beneath lip 26 and inserting connector 18 into receptacle 20.

Figure 3:
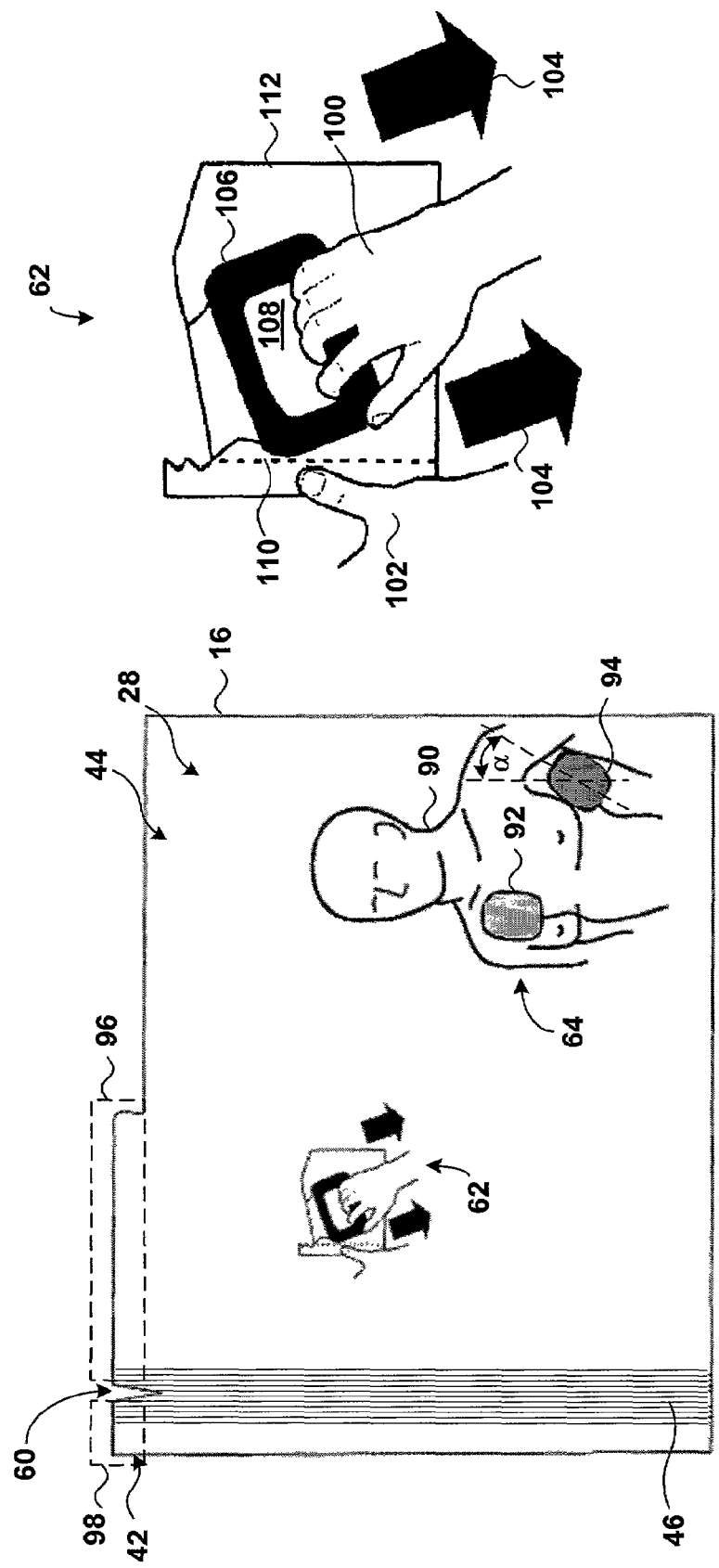
FIG. 3A is a plan view of the obverse face of the pouch.
FIG. 3B is an instructive picture showing a technique for opening the pouch.

An operator desiring to use AED 10 opens cover 12 by depressing button 36 on defibrillator case 14, which releases latch 34. Upon opening AED 10, an operator is immediately presented with the obverse face 44 of pouch 16. Obverse face 44 of pouch 16 includes instructive pictures 28 showing techniques for opening pouch 16 and placing the electrodes on the patient. FIGS. 3A and 3B present examples of instructive pictures 28, and will be described in more detail below.

Electrodes 74 and 76 are hermetically sealed inside pouch 16 to protect electrodes 74 and 76 from the environment. Electrodes 74 and 76 include a hydrogel layer that hydrates the patient's skin, forms an interface with the patient and enhances the capacity of electrodes 74 and 76 to sense electrocardiogram signals from the patient. In addition, the hydrogel promotes adhesion of electrodes 74 and 76 to the skin and reduces the risk of burns to the patient when a defibrillation pulse is applied. Pouch 16 may be, for example, an airtight foil bag that prevents the hydrogel from drying out and losing its desirable properties. Accordingly, the operator must open pouch 16 to obtain access to electrodes 74 and 76.

Pouch 16 includes large handle 24 near upper left corner 42 of pouch 16. Handle 24 may be composed of a brightly colored plastic, such as red plastic, so that handle 24 is especially prominent. Handle 24 may be a ring-type handle as shown in FIG. 1, making handle 24 easy to clutch and pull.

Handle 24 is oriented at an angle relative to defibrillator case 14, suggesting to the operator that handle 24 is to be pulled toward himself and to the right. In addition, handle 24 may include directional arrows 50 that further show the operator the direction in which to pull handle 24. As the operator pulls handle 24, cylindrical member 30 in cylindrical slot 32 anchors upper left corner 42 of pouch 16 in place. Cylindrical member 30 can be removed from cylindrical slot 32 by pulling cylindrical member 30 to the left. However, pulling handle 24 to open pouch 16 will not dislodge cylindrical member 30 from cylindrical slot 32.

The operator tears pouch 16 open by pulling handle 24. Pouch 16 tears beginning at notch 60 (not shown in FIG. 1), and continues to tear along tear strip 46. Tear strip 46 prevents the tear from cutting across pouch 16, potentially damaging electrodes 74 and 76. In one implementation, tear strip 46 comprises tape with embedded fibers that guide the tear. The tape may be included on both the obverse side 44 and the reverse side of pouch 16.

As pouch 16 tears along tear strip 46, pouch opens, making electrodes 74 and 76 accessible. Pouch 16 may be torn into two pieces. The smaller piece is the small strip that remains fastened to defibrillator case 14 by cylindrical member 30. Lead wires 22, which are secured at sealed entry point 48, remain anchored to defibrillator case 14, preventing the operator from inadvertently pulling connector 18 from receptacle 20. The larger piece of pouch 16 slips easily from lip 26. The operator may extract electrodes 74 and 76 from the larger piece, or electrodes 74 and 76 may slip out of the larger piece as the operator pulls handle 24. The operator retrieves electrodes 74 and 76 and, as will be described in more detail below, places electrodes 74 and 76 on the patient.

Figure 2:
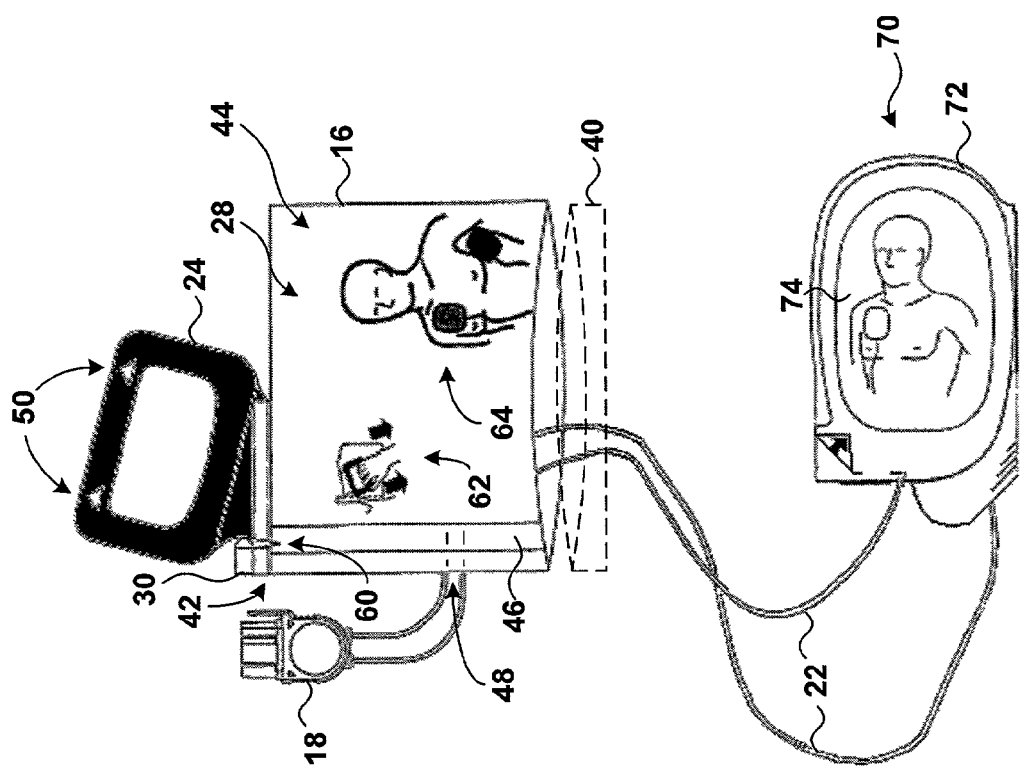
FIG. 2 is a view of a pouch and an electrode assembly.

FIG. 2 shows pouch 16 and electrode assembly 70, which includes a right electrode 74 (also called an anterior electrode) and a left electrode 76 (not shown in FIG. 2) (also called a lateral electrode). Bottom edge 40 of pouch 16 has been removed for purposes of illustration, and FIG. 2 is not intended to demonstrate how electrode assembly 70 is to be removed from pouch 16.

Figure 4:
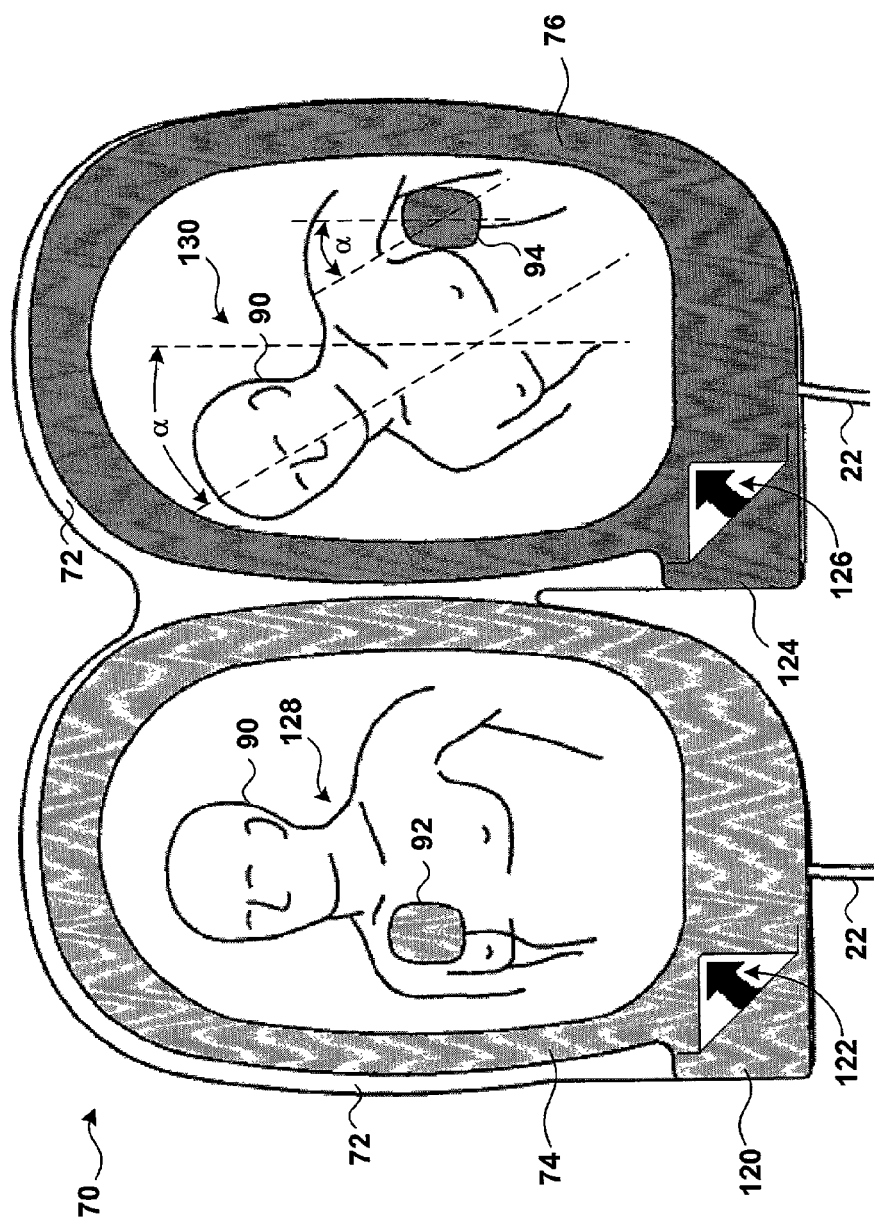
FIG. 4 is a plan view of an electrode assembly.

As shown in FIG. 2 and as will be shown in more detail in FIG. 4, electrode assembly 70 includes right electrode 74 and left electrode 76 affixed to liner 72. Liner 72 is folded to allow electrodes 74 and 76 to fit inside pouch 16. The usefulness of liner 72 will be discussed in more detail in connection with FIG. 4.

FIG. 2 further illustrates that a length of insulated lead wires 22 is coiled inside pouch 16. In one embodiment, about 48 inches (122 cm) of the length of insulated lead wires 22 extends from electrodes 74 and 76 to sealed entry point 48.

FIG. 2 shows cylindrical member 30 and handle 24. Handle 24 has been flipped upward to show obverse face 44 of pouch 16. Cylindrical member 30 and handle 24 are securely bonded to the foil portion of pouch 16, e.g., by ultrasonic welding. Notch 60 is between handle 24 and cylindrical member 30. Notch 60 provides a starting point for tearing of pouch 16. When the operator pulls handle 24 as illustrated in FIG. 3B, pouch 16 tears beginning at notch 60. The portion of pouch 16 to the left side of notch 60 is held in place by cylindrical member 30 in cylindrical slot 32 (not shown in FIG. 2), and the portion to the right side of notch 60 is drawn with handle 24. Pouch 16 tears along tear strip 46.

Obverse face 44 of pouch 16 includes instructive pictures 28. Instructive picture 62 shows the operator how to open pouch 16. Instructive picture 62 is positioned on obverse face 44 to be visible through the opening in handle 24. Instructive picture 64 indicates that pouch 16 contains electrodes and further shows the operator where to place the electrodes on the patient. Instructive pictures 62 and 64 will be discussed in more detail in connection with FIGS. 3A and 3B. In addition, directional arrows 50 on handle 24 may further inform the operator how to pull handle 24.

FIG. 3A shows obverse face 44 of pouch 16. Handle 24 and cylindrical member 30 have been removed. Tab 98 provides a site for securing, cylindrical member 30 to the left of notch 60 and tab 96 provides a site for securing handle 24 to the right of notch 60.

Obverse face 44 of pouch 16 includes instructive pictures 62 and 64. Instructive pictures 62 and 64 may be printed on pouch 16 in many ways, such as by four-color printing or embossing. Instructive pictures 62 and 64 may also be printed labels, for example, that are applied to pouch 16.

Instructive picture 64 depicts bare-chested human FIG. 90, which represents the patient. Right electrode symbol 92 is shown placed on the upper right side of the chest of FIG. 90. Left electrode symbol 94 is shown placed on the lower left side of the chest of FIG. 90. Left electrode symbol 94 is further shown oriented at an angle a, relative to the direction of the head of FIG. 90. Left electrode symbol 94 tells the operator that left electrode 76 should be placed at a small angle. As will be described below in connection with FIG. 4, the angle shown in instructive picture 130 on left electrode 76 assists the operator in making the proper anatomical placement of left electrode 130.

Electrode symbols 92 and 94 are color-coded. The faces of electrodes 74 and 76 are color-coded to match the colors of electrode symbols 92 and 94. The color-coding gives the operator an additional piece of information about correct electrode placement.

FIG. 3B shows instructive picture 62 in more detail. Instructive picture 62 shows the operator how to open pouch 16, represented by pouch symbol 112. In particular, instructive picture 62 includes a handle symbol 106, and shows right hand 100 clutching handle 106 by reaching through opening 108. Handle symbol 106 is color-coded to match the color of handle 24. Left hand 102 is shown holding down pouch 112. Instructive picture 62 further includes directional arrows 104 that show the operator the direction in which to pull handle 24. Instructive picture 62 also shows the tearing of pouch 112 and further shows path 110 along which tearing occurs.

Instructive picture 62 instructs the operator to clutch handle 24 with his right hand. Instructive picture 62 also instructs the operator to hold defibrillator case 14 and the left edge of pouch 16 with his left hand. The left hand provides leverage for opening pouch 16 and prevents the operator from pulling AED 10 when pulling handle 24. Further, instructive picture 62 instructs the operator to pull handle 24 firmly with the right hand, and in particular, to pull toward the operator and to the right, thereby tearing open pouch 16. The orientation of handle 24 and directional arrows 50, as shown in FIGS. 1 and 2, further inform the operator as to pull toward himself and to the right. By applying the techniques illustrated in instructive picture 62, the operator opens pouch 16 and obtains access to electrode assembly 70, including defibrillation electrodes 74 and 76.

FIG. 4 shows electrode assembly 70, including electrodes 74 and 76. Electrodes 74 and 76 may each comprise a tin foil plate on a foam backing. The tin foil plates (not shown in FIG. 4) are electrically coupled to lead wires 22. Right electrode 74 is color-coded to match right electrode symbol 92, and left electrode 76 is color-coded to match left electrode symbol 94. Electrodes 74 and 76 are affixed in a non-permanent fashion to liner 72.

As noted above, the tin foil plates of electrodes 74 and 76 are coated with a hydrogel that promotes adhesion of electrodes 74 and 76 to the patient's skin. Electrodes 74 and 76 may also include additional adhesives to promote adhesion. Liner 72 prevents electrodes 74 and 76 from sticking to each other. The operator must remove liner 72 from electrodes 74 and 76 before applying electrodes 74 and 76 to the patient.

Electrode assembly 70 includes features to instruct the operator to remove electrodes 74 and 76 from liner 72. Right electrode 74 includes tab 120 with peeled-corner icon 122, instructing the operator to peel right electrode 74 from liner 72. Similarly, left electrode 76 includes tab 124 with peeled-corner icon 126 that instructs the operator to peel left electrode 76 from liner 72. Peeled-corner icons resemble a flipped-up corner of tabs 120 and 124, along with directional arrows that show the operator how to remove electrodes 74 and 76 from liner 72.

Further, a single liner 72 adheres to both electrodes 74 and 76. Use of one liner 72 helps the operator understand that liner 72 needs to be removed from both electrodes 74 and 76. In particular, electrodes 74 and 76 include instructive pictures 128 and 130, which may be printed on electrodes 74 and 76 using a variety of techniques. Instructive pictures 128 and 130 are similar to instructive picture 64 on obverse face 44 of pouch 16. Unlike instructive picture 64, which includes symbols for right and left electrodes 92 and 94, instructive picture 128 includes only right electrode symbol 92 and instructive picture 130 includes only left electrode symbol 94. Instructive pictures 64, 128 and 130 instruct the operator that electrodes 74 and 76 must be placed some distance apart on the chest of the patient.

It is immediately apparent to the operator that electrodes 74 and 76 cannot be placed in the designated locations unless electrodes 74 and 76 are separated. As liner 72 is not perforated and cannot be easily torn, it is evident to the operator that electrodes 74 and 76 may be separated by removal of liner 72. Tabs 120 and 124 with peeled-corner icons 122 and 126 reinforce this correct conclusion. Accordingly, the operator recognizes that electrodes 74 and 76 can be separated by removing them from liner 72.

Moreover, liner 72 may be color-coded so as not to match any symbol in instructive pictures 62, 64, 128 or 130. Liner 72 may be blue, for example, and instructive pictures 62, 64, 128 and 130 may include no items that are blue. When the operator encounters blue liner 72, and sees no blue items in instructive pictures 62, 64, 128 and 130, the operator is led to the correct conclusion that liner 72 is to be removed and discarded. Color-coding also provides contrast, so that the operator understands that liner 72 is distinct from electrodes 74 and 76.

Instructive picture 128 shows the correct placement of right electrode 74. In particular, instructive picture 128 shows right electrode symbol placed upon the right side of the chest of human FIG. 90, above and slightly to the left of the right nipple. When right electrode 74 is correctly placed, instructive picture 128 appears properly oriented, in that the head of FIG. 90 is oriented in the same direction as the head of the patient.

On the face of left electrode 76, FIG. 90 in instructive picture 130 is oriented at an angle $\alpha$, as compared with the orientation of FIG. 90 in instructive picture 128. As FIG. 4 illustrates, the same angle α describes the orientation of left electrode symbol 94 relative to the direction of the head of FIG. 90 in instructive pictures 64 and 130.

Orientation of FIG. 90 in instructive picture 130 at angle α demonstrates to the operator the proper placement of left electrode 76. In particular, when the operator correctly places left electrode 76, instructive picture 130 appears to the operator to be properly oriented, with the head of FIG. 90 oriented in the same direction as the head of the patient.

To place left electrode 76 in the correct orientation, the operator turns left electrode 76 by approximately angle α prior to placement. In particular, the operator orients the head of FIG. 90 in the same direction as the head of the patient. In doing so, the operator places left electrode 76 in the orientation resembling the orientation of left electrode symbol 94 in instructive picture 64.

The angled placement of left electrode 76 may provide therapeutic benefit to the patient. In defibrillation, AED 10 supplies current that travels between electrode 74 and 76. The current, intended to depolarize the heart of the patient, should flow across the heart of the patient, approximately along a line from the sinoatrial node to the apex of the heart. Right electrode 74 and left electrode 76 are placed on opposite ends of this line, with left electrode 76 positioned on the lower chest of the patient and somewhat on the side of the chest. Angled placement of left electrode 76 is more likely to produce proper anatomical placement, and is therefore more likely to result in proper current flow.

Once the operator has placed the electrodes on the chest of the patient, AED 10 may automatically sense the presence of a conductive path through the body of the patient. AED 10 may evaluate the heart rhythm of the patient and may deliver a shock when a shockable rhythm is detected. In some AED's, the AED administers the shock automatically, and in others, the AED cues the operator to press a button to administer the shock.

AED 10 cannot evaluate the heart rhythm until the defibrillation electrodes 74 and 76 are placed, and the efficacy of the shock is dependent upon proper electrode placement on the patient's chest. Accordingly, the burden is on the operator, who may have little formal training in the use of the AED or may have had training a long time ago, to retrieve the electrodes and place the electrodes at the correct sites on the chest of the patient. In addition, the operator must perform these actions quickly.

The invention assists the operator in performing these tasks in several respects. The invention provides for easy-opening pouch 16, which tears open upon the pull of handle 24. Several visual cues prompt the operator to pull handle 24. Handle 24 is a prominent feature of pouch 16, may be brightly colored and may include directional arrows 50. In addition, instructive picture 62 shows the operator that pouch 16 is to be opened, and further shows the operator how to perform this task. An anchor such as cylindrical member 30 holds a corner of pouch 16 in place, making it easier for the operator to open pouch 16 by pulling handle 24.

Once pouch 16 is open, the operator extracts electrode assembly 70, including defibrillation electrodes 74 and 76 mounted on liner 72. Several visual cues prompt the operator to remove liner 72 and place electrodes 74 and 76 on the patient. Tabs 120 and 124 and peeled-corner icons 122 and 126 prompt the operator to peel electrodes 74 and 76 from liner 72. Instructive picture 64 on pouch 16, instructive picture 128 on right electrode 74 and instructive picture 130 on left electrode 76 show the operator where to place electrodes 74 and 76. Color-coding of electrodes 74 and 76, which matches the color-coding of electrode symbols 92 and 94 in instructive pictures 64, 128 and 130, helps the operator distinguish right electrode 74 from left electrode 76 and helps the operator place electrodes 74 and 76 in the correct sites. The angled orientation of human FIG. 90 in instructive picture 130 further helps the operator position left electrode 76 properly.

In summary, there are several visual cues that show the operator what needs to be done. Many visual cues, such as directional arrows 50 and directional arrows 104, reinforce the same actions. Commonly known and understood symbols such as human figures and arrows make instructive pictures 62, 64, 128 and 130 easily understood by an operator. Explanatory text may be completely absent from AED 10. Instead of spending time reading detailed directions, the operator follows the visual cues. In addition, because instructive pictures 62, 64, 128 and 130 need no explanatory text, there is no language barrier.

As a result, the operator places electrodes 74 and 76 on the patient in a short period of time. The more quickly the operator places electrodes 74 and 76, the greater the likelihood that AED 10 will provide successful treatment for the patient.

Various embodiments of the invention have been described. These embodiments are illustrative of the practice of the invention. Various modifications may be made without departing from the scope of the claims. For example, the handle may be constructed other than shown in FIGS. 1 and 2. The handle may, for example, be formed from the same foil material as the pouch. A handle may be presented in a form other than a ring, such as a cord, a knob or a lever.

Many different forms of anchors are also possible, such as a clip, an adhesive or a hook. Although the embodiments described above show an anchor in the form of a cylindrical member 30 that mates with cylindrical slot 32, an anchor may include other forms of mating members on pouch 16 and defibrillator case 14. In addition, the invention encompasses embodiments in which the anchor is a component of defibrillator case 14, with no mating member on pouch 16. Defibrillator case 14 may include, for example, a clasp that fastens pouch 16 to case 14. Similarly, the invention encompasses embodiments in which the anchor is a component of pouch 16, with no mating member on defibrillator case 14.

Modifications may also be made to the electrode assembly or the electrodes without departing from the scope of the claims. For example, both defibrillation electrodes need not be mounted on a single liner, as shown in FIG. 4. Instead, each electrode may be mounted on its own liner. The electrodes may include visual cues other than tabs and arrows that tell the operator to remove the liner.

The instructive pictures on the pouch and electrodes need not be line drawings. Other visual information, such as photographs, may also be employed. Although the invention instructs the operator with no written explanatory text, the invention also encompasses embodiments having written instructions on the AED, the pouch, the electrodes, or elsewhere. The invention further encompasses embodiments in which instructions are provided audibly or with a visual display.

Furthermore, the invention may be practiced with a variety or medical devices and is not limited to an AED. The invention may be practiced, for example, with a defibrillator-monitor, which may be used to display the heart rhythm of the patient on an LCD screen, CRT screen or other display. A defibrillator-monitor may deliver a defibrillation shock when needed, but a defibrillator-monitor may also be used for monitoring or diagnostic purposes.

These and other embodiments are within the scope of the following claims.

The invention claimed is:

1. A device comprising:
   a defibrillation electrode defining a first medial axis within a plane of a surface of the defibrillation electrode;
   a human figure printed on the surface of the defibrillation electrode, the human figure defining a second medial axis within a plane of the human figure on the surface of the defibrillation electrode; and
   an electrode symbol printed on the human figure,
   wherein the human figure is oriented on the defibrillation electrode such that the second medial axis of the human figure is positioned at an angle relative to the first medial axis of the defibrillation electrode, wherein the angle is non-zero such that when the defibrillation electrode is applied to a patient with the head of the patient and the head of the human figure in the same direction, the second medial axis will be substantially parallel to a corresponding medial axis of the patient, wherein the angle defines proper placement of the defibrillation electrode on the patient for defibrillation therapy.

2. The device of claim 1, wherein the second medial axis of the human figure is oriented relative to the first medial axis on the defibrillation electrode at the angle so that when the defibrillation electrode is applied to a left side of the chest of the patient with the head of the patient and the head of the human figure in the same direction, the second medial axis will be substantially parallel to the corresponding medial axis of the patient and the defibrillation electrode will be properly placed on the left side of the chest of the patient for defilation therapy.

3. The device of claim 1, wherein the defibrillation electrode is a left defibrillation electrode, the device further comprising:
   a right defibrillation electrode; and
   a liner affixed to the left defibrillation electrode and the right defibrillation electrode.

4. The device of claim 3, wherein the color of the liner is distinct from the colors of the left and right defibrillation electrodes.

5. The device of claim 1, further comprising:
   a liner affixed to the defibrillation electrode; and
   an icon printed on the defibrillation electrode that illustrates peeling the defibrillation electrode from the liner.

6. The device of claim 1, wherein the defibrillation electrode is a left defibrillation electrode, the device further comprising:
   a right defibrillation electrode;
   a second human figure printed on the right defibrillation electrode; and
   a right electrode symbol printed on the second human figure.

7. A method comprising:
   printing a human figure on a defibrillation electrode, wherein the defibrillation electrode defines a first medial axis within a plane defined by a surface of the defibrillation electrode and wherein the human figure defines a second medial within a plane defined by the human figure on the defibrillation electrode; and
   printing the human figure to include an electrode symbol on the human figure,
   wherein the human figure is oriented on the defibrillation electrode such that the second medial axis of the human figure is positioned at an angle relative to the first medial axis of the defibrillation electrode, wherein the angle is non-zero such that when the defibrillation electrode is applied to a patient with the head of the patient and the head of the human figure in the same direction, the second medial axis of the human figure will be substantially parallel to a corresponding medial axis of the patient, wherein the angle defines proper placement of the defibrillation electrode on the patient for defibrillation therapy.

8. The method of claim 7, wherein the second medial axis of the human figure is oriented relative to the first medial axis on the defibrillation electrode at the angle so that when the defibrillation electrode is applied to a left side of the chest of the patient with the head of the patient and the head of the human figure in the same direction, the second medial axis will be substantially parallel to a corresponding medial axis of the patient and the defibrillation electrode will be properly placed on the left side of the chest of the patient for defilation therapy.

9. The method of claim 7, wherein the defibrillation electrode is a left defibrillation electrode, the method further comprising:
   affixing the left defibrillation electrode and a right defibrillation electrode to a liner.

10. The method of claim 9, further comprising printing an icon on the left defibrillation electrode that illustrates peeling the left defibrillation electrode from the liner.

11. The method of claim 9, wherein the color of the liner is distinct from the colors of the left and right defibrillation electrodes.

12. The method of claim 7, wherein the defibrillation electrode is a left defibrillation electrode, the method further comprising:
   printing the human figure on a right defibrillation electrode; and
   printing a right electrode symbol on the human figure on the right defibrillation electrode.

13. A device comprising:
   a right defibrillation electrode comprising a medial axis within a plane of a surface of the right defibrillation electrode and including a first instructive picture; and
   a left defibrillation electrode comprising a medial axis within a plane of a surface of the left defibrillation electrode and including a second instructive picture,
   wherein the first instructive picture includes a right electrode symbol on a first human figure, the first human figure comprising a medial axis oriented substantially parallel to the medial axis of the right defibrillation electrode, and
   wherein the second instructive picture includes a left electrode symbol on a second human figure, the second human figure comprising a medial axis oriented substantially non-parallel to the medial axis of the the left defibrillation electrode.

14. The device of claim 13, further comprising a liner affixed to the right defibrillation electrode and the left defibrillation electrode.

15. The device of claim 14, wherein the color of the liner is distinct from the colors of the left and right defibrillation electrodes.

16. The device of claim 13, wherein at least a portion of the right electrode includes a first color, at least a portion of the left electrode includes a second color, the right electrode symbol includes the first color and not the second color and the left electrode symbol includes the second color and not the first color.

17. The device of claim 13, wherein the first and second human figures are oriented on the left defibrillation electrodes such that when the first and second defibrillation electrodes are properly placed on a patient for defibrillation therapy, the medial axes of the defibrillation electrodes will be substantially non-parallel with one another and medial axes of the first and second human figures will be substantially parallel to a corresponding medial axis of the patient.

* * * * *

UNITED STATES PATENT AND TRADEMARK OFFICE
CERTIFICATE OF CORRECTION

| | | |
|---|---|---|
| PATENT NO. | : 7,069,074 B2 | Page 1 of 1 |
| APPLICATION NO. | : 10/008243 | |
| DATED | : June 27, 2006 | |
| INVENTOR(S) | : Kevin Kelly Covey et al. | |

It is certified that error appears in the above-identified patent and that said Letters Patent is hereby corrected as shown below:

In column 6, line 41, delete "tom," and insert -- torn, --, therefore.

In column 10, line 54, in claim 13, before "left" delete "the".

In column 11, line 2, in claim 17, delete "left" and insert -- right and left --, therefor.

In column 11, line 5, in claim 17, delete "axes" and insert -- axis --, therefor.

In column 12, line 2, in claim 17, delete "axes" and insert -- axis --, therefor.

Signed and Sealed this

Seventeenth Day of August, 2010

David J. Kappos
*Director of the United States Patent and Trademark Office*